US005921234A

United States Patent [19]
Garofalo

[11] Patent Number: 5,921,234

[45] Date of Patent: Jul. 13, 1999

[54] FIRST REDUCING STAGE FOR TWO-STAGE BREATHING APPARATUS

[75] Inventor: Giovanni Garofalo, Rapallo, Italy

[73] Assignee: HTM Sport S.p.A., Italy

[21] Appl. No.: 08/965,795

[22] Filed: Nov. 7, 1997

[30] Foreign Application Priority Data

Nov. 8, 1996 [IT] Italy ............................ GE 9600036 U

[51] Int. Cl.[6] .................................................... A61M 16/00

[52] U.S. Cl. ................................ 128/201.28; 128/205.24

[58] Field of Search ......................... 128/201.28, 204.26, 128/205.24, 201.27

[56] References Cited

U.S. PATENT DOCUMENTS

| | | | |
|---|---|---|---|
| 4,176,418 | 12/1979 | Scott | 128/204.24 |
| 4,449,524 | 5/1984 | Gray | 128/204.26 |
| 4,840,199 | 6/1989 | Brunt, Jr. | 128/205.24 |
| 5,184,609 | 2/1993 | Hart | 128/205.24 |
| 5,190,030 | 3/1993 | Semeia | 128/201.28 |
| 5,318,019 | 6/1994 | Cleaya | 128/204.26 |
| 5,379,761 | 1/1995 | Schuler | 128/204.26 |
| 5,411,018 | 5/1995 | Rinehart | 128/204.26 |
| 5,413,096 | 5/1995 | Hart | 128/205.24 |
| 5,509,407 | 4/1996 | Schuler | 128/204.26 |
| 5,584,289 | 12/1996 | Wise | 128/205.24 |
| 5,655,524 | 8/1997 | Atkins | 128/204.26 |
| 5,687,712 | 11/1997 | Semeia | 128/205.24 |
| 5,746,198 | 5/1998 | Taba et al. | 128/205.24 |
| 5,755,224 | 5/1998 | Good et al. | 128/205.24 |

FOREIGN PATENT DOCUMENTS

| | | |
|---|---|---|
| 0310738 | 4/1989 | European Pat. Off. . |
| 0522913 | 1/1993 | European Pat. Off. . |
| 95/03092 | 2/1995 | WIPO . |

*Primary Examiner*—Aaron J. Lewis
*Attorney, Agent, or Firm*—Larson & Taylor

[57] ABSTRACT

A first reducing stage for a two-stage breathing apparatus includes a metal body having at least one inlet for the compressed air coming from the cylinder or cylinders and a plurality of outlets for the air at a reduced pressure. The body is enclosed in a casing having suitable apertures providing access to the inlet and to the outlets.

4 Claims, 2 Drawing Sheets

FIRST REDUCING STAGE FOR TWO-STAGE BREATHING APPARATUS

FIELD OF THE INVENTION

The present invention relates to underwater breathing apparatus, and in particular relates to first reducing stages for two-stage breathing apparatus.

BACKGROUND OF THE INVENTION

The first reducing stage of a two-stage regulator generally comprises a metal body in which the pressure reducing device is located. The body has at least one inlet for the compressed air coming from the cylinder or cylinders and a plurality of outlets for the air at a reduced pressure. This device, which is connected to the cylinders, is usually found near the nape of the diver's neck; the diver is, therefore, vulnerable to being struck accidentally by the reducing valve. What is more, the reducing valve itself is in turn exposed to accidental knocks from the underwater environment, for example being struck by rocks or bits of wreckage which can damage it, sometimes even seriously.

SUMMARY OF THE INVENTION

The object of the present invention is to provide suitable protection which effectively protects both the diver and the first reducing stage of an underwater breathing apparatus.

The object of the present invention is, therefore, a first reducing stage for two-stage breathing apparatus comprising a metal body having at least one inlet for the compressed air coming from the cylinder or cylinders and a plurality of outlets for the air at a reduced pressure, in which the body is enclosed in a casing, preferably made from an impact-resistant material such as a plastic, having suitable apertures providing access to the inlet and to the outlets.

BRIEF DESCRIPTION OF THE DRAWINGS

Additional advantages and features will be apparent from the following description of an embodiment of the present invention which is given, by way of non-limiting example, with reference to the appended drawings, in which.

DESCRIPTION OF THE PREFERRED EMBODIMENT

Figure 1:
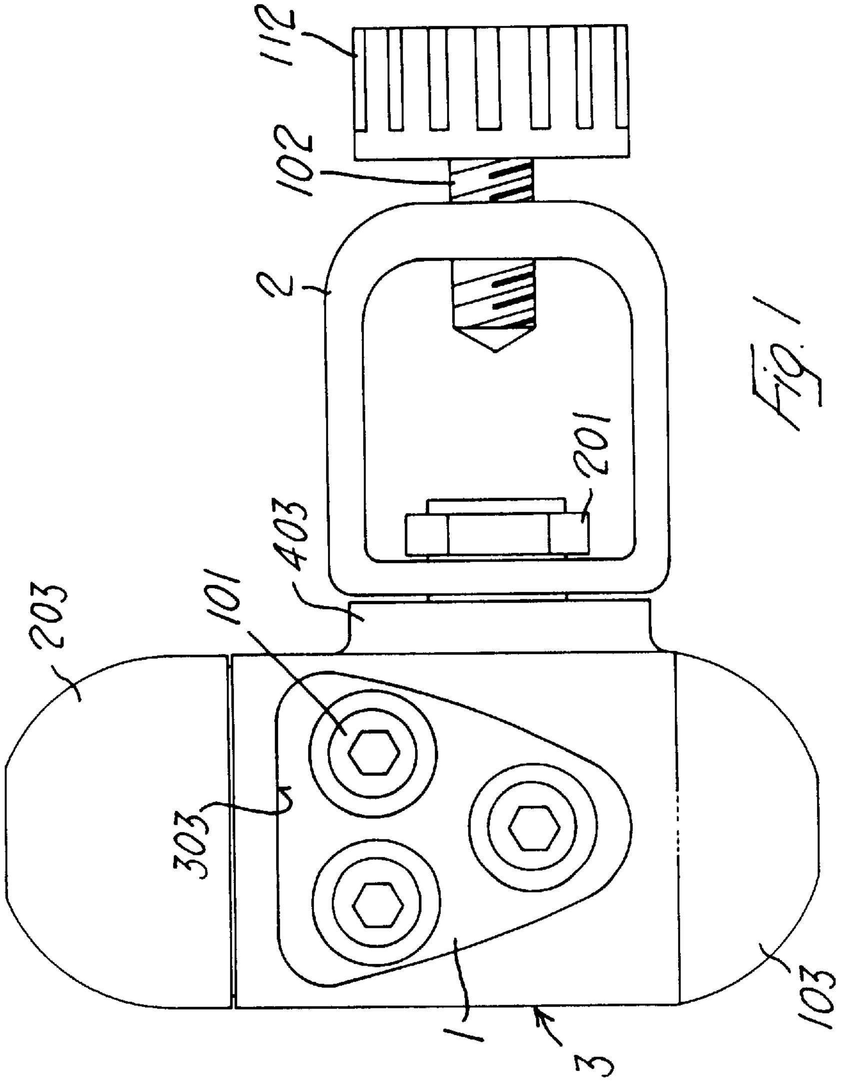
FIG. 1 is a front view of the reducing valve according to the present invention.

FIG. 1 illustrates a first reducing stage, hereinafter referred to as the reducing valve, of a type known per se and not described in greater detail as far as its operation is concerned; first reducing stages for two-stage breathing apparatus of this type are for example disclosed in documents such as WO 95/03092; EP-A0310738 and EP-A-0522913. In the figure, the reference numerals 1 denotes the body of the said reducing valve. This body comprises the low pressure outlets 101 and an inlet 201, to which is connected the yoke 2 provided with a screw 102 fitted with a wheel 112, for closing off the valve of a compressed air cylinder (not shown in the figure). The body 1 is covered by the casing 3 comprising a container element 103 which has an opening 303 formed around the outlets 101 of the body 1 and a sleeve 403 through which the inlet 201 of the said body 1 passes. The casing also comprises a lid 203 which is connected to the said container element 103.

Figure 2:
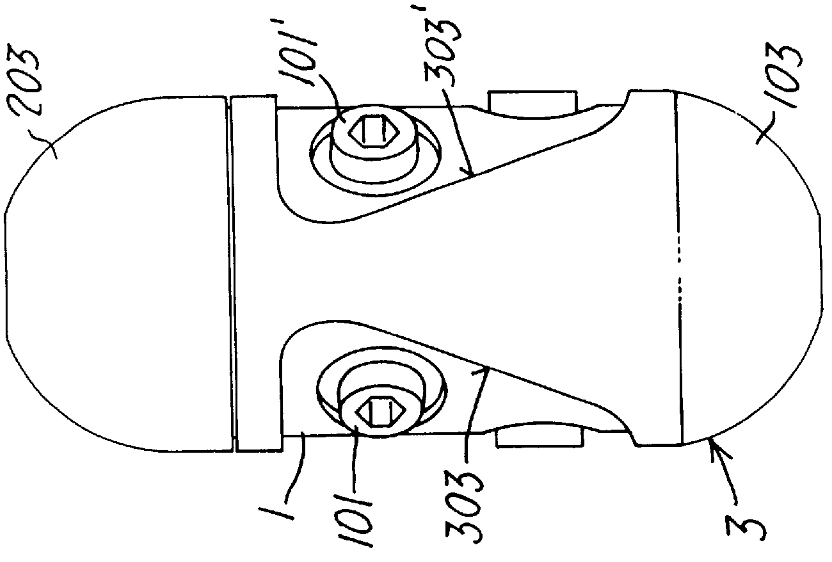
FIG. 2 is a side view of the reducing valve illustrated in FIG. 1.

FIG. 2 illustrates how, given that outlets 101' are located diametrically opposite the outlets 101 in the external side wall of the said body 1 of the reducing valve, the container element 103 of the casing 3 consequently also has an opening 303' around the outlets 101'.

Figure 3:
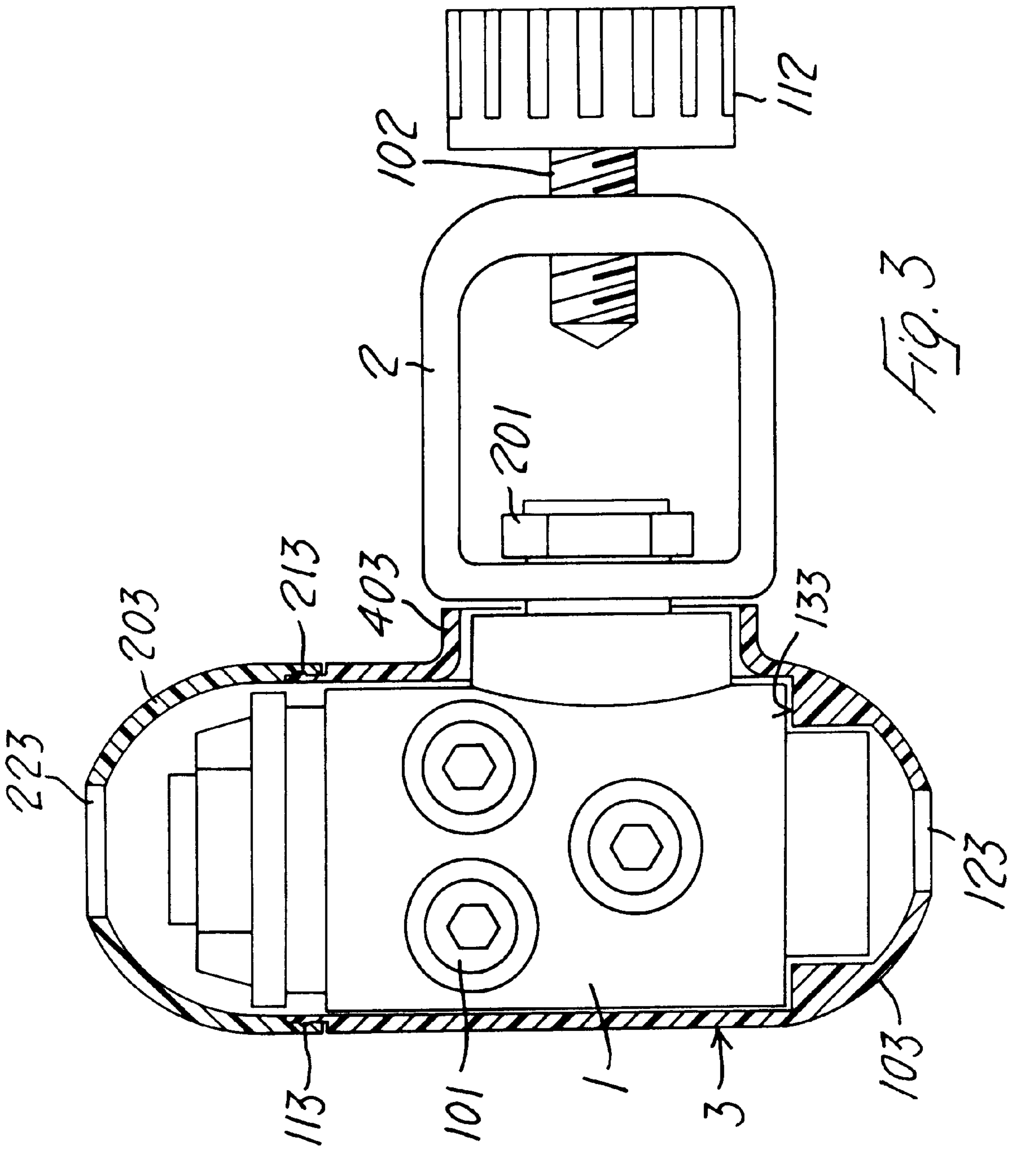
FIG. 3 is a view similar to that in FIG. 1, showing some parts in longitudinal section.

FIG. 3 shows the casing 3 in longitudinal section. As can be seen in the figure, the lid 203 and the container element 103 fit together by means of the annular ridge 113 found on the external peripheral edge of the open end of the container element 103 engaging inside the groove 213 in the internal peripheral edge of the lid 203. The lid 203 has a hole 223 centered on its longitudinal axis, with a similar hole 123 being similarly positioned at the opposite end of the container element 103 to the open end. A shoulder 133, on which the body 1 of the reducing valve rests, is formed on the internal surface of the element 103, close to the hole 123.

The way in which the device according to the present invention works will be evident from the following description. The casing 3 is fitted over the body 1 of the reducing valve prior to the inlet 201 being inserted into the body 1 and the corresponding yoke 2 being fixed. The casing is formed in two parts so as to allow access to the body 1 of the regulator. Furthermore, the holes 123 and 223 are formed so that the reducing valve can be in communication with the external environment. Lastly, the shoulder 133 formed inside the container element 103 means that the body 1/casing 3 assembly is more stable.

The casing 3 of the body 1 of the reducing valve is made such that it covers the body 1 as tightly as possible and is also rounded so that if it does accidentally strike the back of the diver's neck, it has as few sharp edges as possible. The casing is made from an impact-resistant material, in particular a plastic such as a high-strength, high-performance polymer.

The first reducing stage designed according to the present invention is thus safer for the diver to use and is also better protected against accidental contact that could cause possibly serious damage to its structure.

What I claim is:

1. A first reducing stage for a two-stage breathing apparatus comprising a metal body having at least one inlet for compressed air coming from at least one cylinder and a plurality of outlets for air at a reduced pressure, and further comprising a casing comprising a container element and a lid connectable to the container by coupling means, the casing having suitable apertures providing access to the inlet and to the outlets, the casing enclosing the body and fitting tightly over the external surface of the body.

2. First reducing stage according to claim 1, wherein the said casing has at least one through hole.

3. First reducing stage according to claim 2, wherein the casing is made from a plastic material, preferably a high-performance polymer.

4. First reducing stage according to claim 3, wherein the external surface of casing is rounded.

* * * * *